US00PP35636P2

(12) United States Plant Patent
Thomson et al.

(10) Patent No.: US PP35,636 P2
(45) Date of Patent: Feb. 6, 2024

(54) ***PASSIFLORA* PLANT NAMED 'WELLINGTON 101'**

(50) Latin Name: *Passiflora edulis*
Varietal Denomination: Wellington 101

(71) Applicants: Angus Philip Thomson, Western Cape (ZA); Johannes Petrus Swart, Western Cape (ZA)

(72) Inventors: Angus Philip Thomson, Western Cape (ZA); Johannes Petrus Swart, Western Cape (ZA)

( * ) Notice: Subject to any disclaimer, the term of this patent is extended or adjusted under 35 U.S.C. 154(b) by 0 days.

(21) Appl. No.: 18/216,740

(22) Filed: Jun. 30, 2023

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./156, 226
See application file for complete search history.

(56) References Cited

U.S. PATENT DOCUMENTS

PP35,408 P2 * 10/2023 Alvarez Ramirez ..... Plt./156

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct cultivar of *Passiflora* plant, referred to by its cultivar name, 'Wellington 101', is disclosed. The new cultivar is characterized by its large white flowers consisting of white petals, green sepals, and deep purple colored corona filaments, dark-green-colored foliage, large round fruit with orange flesh, and moderately vigorous, vining growth habit.

2 Drawing Sheets

Latin name of genus and species of plant claimed: *Passiflora edulis*.

Variety denomination: 'Wellington 101'.

STATEMENT REGARDING PRIOR DISCLOSURES BY THE INVENTOR

The first offer for sale of the new variety was Jul. 8, 2022, from South Africa to Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The present invention relates to a new and distinct cultivar of *Passiflora* plant botanically known as *Passiflora edulis* and hereinafter referred to by the cultivar name 'Wellington 101'.

The new cultivar originated in a controlled breeding program in Citrusdal, Swart Farm, Western Cape, South Africa during Summer 2014. The objective of the breeding program was the development of superior *Passiflora* cultivars for commercial farming. The new *Passiflora* cultivar is the result of cross-pollination. The female parent (i.e., the seed parent) of the new cultivar is *Passiflora* 'Ester' (not patented). The male parent (i.e., the pollen parent) of the new cultivar is *Passiflora* 'Mariana' (not patented).

The parentage of the new cultivar can be summarized as follows:

'Ester' X 'Mariana'

The seeds resulting from the above pollination were sown and small plants were obtained which were physically and biologically different from each other. The new cultivar was discovered and selected as a single flowering plant within the progeny of the above stated cross-pollination during May 2015 in a controlled environment in Citrusdal, Western Cape, South Africa.

The new variety has been found to undergo asexual propagation in Citrusdal, Western Cape, South Africa by cuttings since September 2016. Asexual propagation has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Wellington 101' as a new and distinct cultivar of *Passiflora* plant:

(a) Large white flowers consisting of white petals, green sepals, and deep purple colored corona filaments,
(b) Dark green colored foliage,
(c) Large round fruit with orange flesh, and
(d) A moderately vigorous, vining growth habit.

The new variety of the present invention can be readily distinguished from its ancestors. More specifically, the new cultivar produces larger fruit with more flesh and a more controlled growth habit compared to the 'Ester' variety (i.e., the seed parent). In addition, the new cultivar produces smaller fruit with more flesh and a more vigorous growth habit compared to the 'Mariana' variety (i.e., the pollen parent). Moreover, the new cultivar can be readily distinguish from other similar non-parental varieties. Of the many commercially available *Passiflora* cultivars, the most similar in comparison to the new cultivar is the 'Black Knight' variety (not patented). However, plants of the new cultivar differ from plants of 'Black Knight'. For example, plants of the new cultivar express a more compact growth habit compared to plants of 'Black Knight'; the new cultivar forms leaves that are lighter green in color compared to the leaves formed on plants of 'Black Knight'; and the new cultivar produces fruit that is more rounded in shape with more flesh and sap compared to the fruit produced by plants of 'Black Knight'.

BRIEF DESCRIPTION OF THE PHOTOGRAPHS

The accompanying photographs show, as nearly true as it is reasonably possible to make the same in color illustrations of this type, a typical container grown plant of the new variety. The illustrated *Passiflora* plant of the new variety was approximately two years of age and was grown in Cochranville, PA and observed in February 2023.

DETAILED BOTANICAL DESCRIPTION

Figure 1:
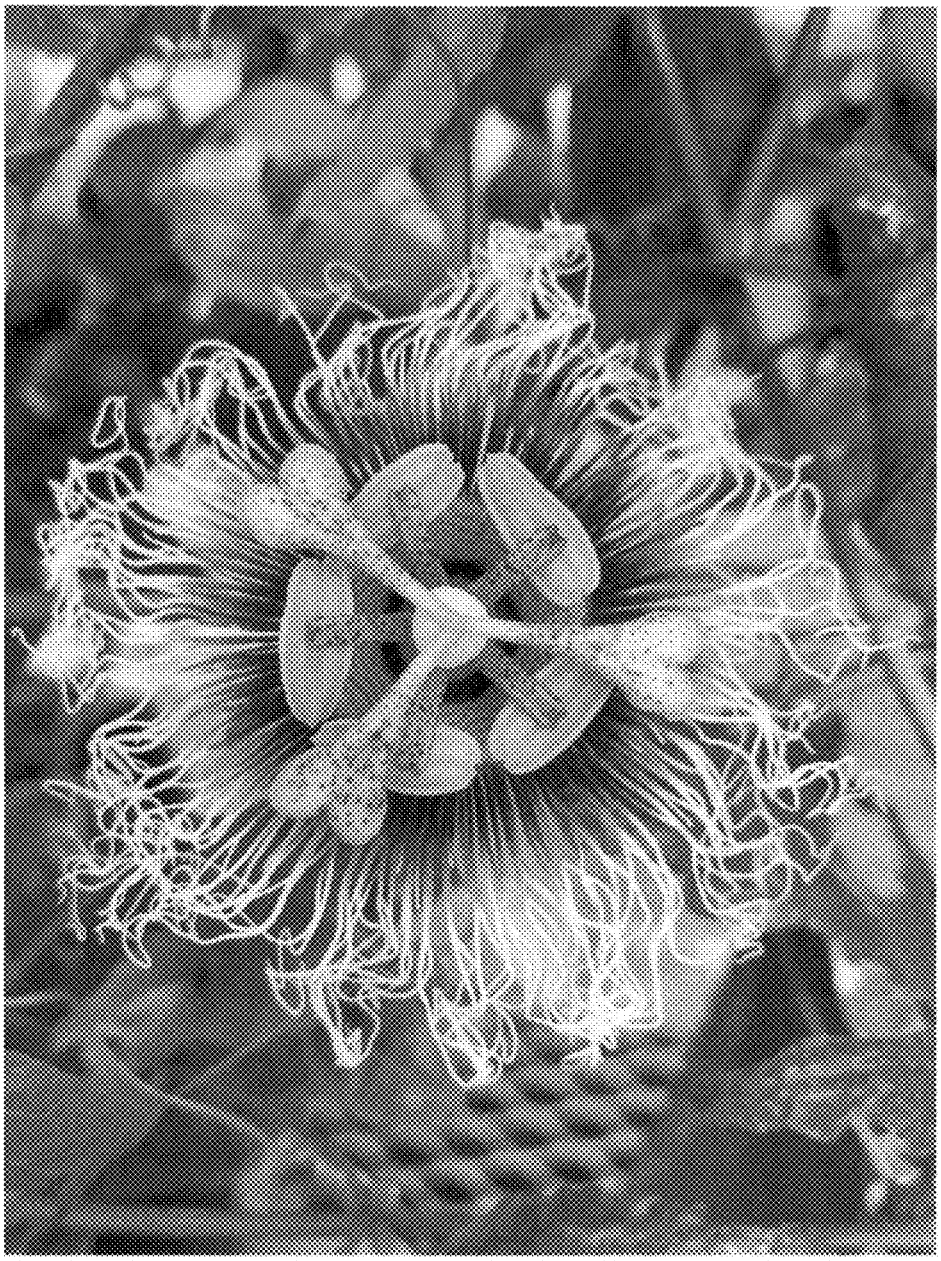
FIG. 1 illustrates a flower, close up view, of 'Wellington 101'
Figure 2:
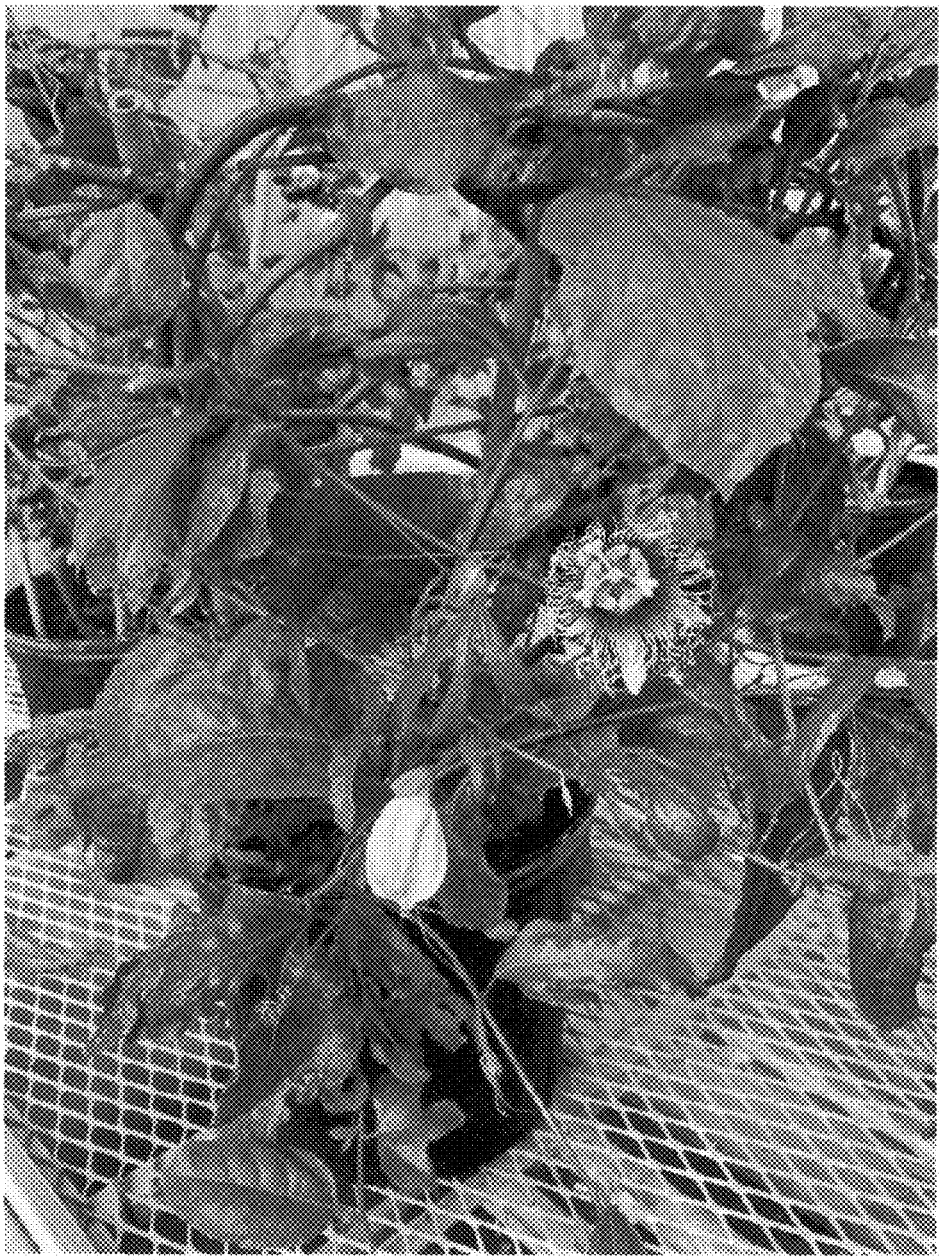
FIG. 2 illustrates a side view of 'Wellington 101'

The chart used in the identification of colors described herein is The R.H.S. Colour Chart of The Royal Horticultural Society, London, England, 2015 edition, except where general color terms of ordinary significance are used. The color values were determined in February 2023 under natural light conditions in Cochranville, Pennsylvania of two-years old specimens of the new variety.

Measurements and numerical values represent averages of typical plants, which were approximately two years of age and grown in Cochranville, Pennsylvania in February 2023.

Botanical classification: *Passiflora edulis* 'Wellington101'.

Parentage:

*Female parent.*—'Ester' (not patented).

*Male parent.*—'Mariana' (not patented).

Propagation:

*Type cutting.*—Softwood cuttings.

*Time to initiate roots.*—Approximately 22 days.

*Time to produce a rooted cutting.*—Approximately 51 days.

*Root description.*—Slightly fleshy, white in color and strong.

*Rooting habit.*—Freely branching.

Plant description:

*Commercial crop time.*—Approximately 8 months to finish in a 3-gallon container from a rooted plug and approximately 4 months to finish in a 1-gallon container from a rooted plug.

*Growth habit and general appearance.*—Moderately vigorous, compact, and vining growth habit.

*Hardiness.*—USDA Zone 7 (0° F. to 10° F.).

*Size.*—Height from soil level to top of plant plane: Approximately 60.0 cm. Width: Approximately 50.0 cm.

*Branching characteristics.*—Freely branching. Pinching enhances branching. Approximately 10 primary branches from center of plant, angled approximately 75 degrees from center of plant. Each primary branch has 4 to 10 lateral branches.

*Primary branches.*—Strength: Very Strong, difficult to break. Length: Typically between 30.0 to 45.0 cm. Primary Branch Diameter: Approximately 5.0 mm. Primary Branch Color: Commonly near Green Group 139A, with age, covered with a thin bark like layer colored near Greyed-Green Group N199B. Primary Branch Texture: Young growth hirsute, hairs, approximately 1.5 mm long, colored near Yellow-Green Group 145D. Older growth is scaly, hirsute. Hair color commonly near White Group 155D.

*Secondary branches.*—Strength: Very Strong, flexible. Number of Lateral Branches: Approximately 4 to 10 per primary branch. Length: Approximately 14.0 cm. Secondary Branch Diameter: Approximately 3.0 mm. Secondary Branch Color: Commonly near Yellow-Green Group N144A. Lateral Branch Texture: Hirsute. Internode Length: Between 2.0 mm and 6.0 cm.

Foliage description:

*General description.*—Fragrance: None detected. Type: Compound, predominantly 3-lobed, occasionally 1-lobed. Arrangement: Alternate.

*Leaves.*—Shape: Multilobed. Length of entire compound leaf: Approximately 17.0 cm. Width of entire compound leaf: Approximately 19.5 cm. Central lobe length: Approximately 17.0 cm. Central lobe width: Approximately 6.0 cm. Outer lobe length: Approximately 12.0 cm. Outer lobe width: Approximately 4.0 cm. Margin: Entire. Apex: Acute. Base: Fused to adjacent lobes. Venation pattern: Palmate. Texture of upper surface: Glabrous. Texture of lower surface: Glabrous. Color of upper surface of young foliage: Commonly near Green Group 141B with indistinguishable venation. Color of lower surface of young foliage: Commonly near Yellow-Green Group 146D with indistinguishable venation. Color of upper surface of mature foliage: Commonly near Green Group 139A with venation of near Yellow-Green Group 153D. Color of lower surface of mature foliage: Commonly near Green Group 138A with venation of near Yellow-Green Group 151A.

*Petiole.*—Length: Approximately 1.5 cm. Diameter: Approximately 3.0 mm. Color or upper and lower surfaces: Commonly near Yellow-Green Group 144A.

*Stipules.*—Length: Approximately 3.0 cm. Diameter: Approximately 1.5 cm. Color or upper and lower surfaces: Commonly near Yellow-Green Group 146A.

*Tendrils.*—Length: Approximately 17.0-20.0 cm. Diameter: Approximately 2.0 mm. Color: vary in color from between near Yellow-Green Group 146B and near Greyed-Orange Group 175D.

Flowering description:

*Flowering season.*—Flowers in spring and continues to produce flowers throughout Summer and Fall. Flowering ends with the onset of frost.

*Lastingness of individual inflorescence on the plant.*—Approximately 2 to 3 days.

Flower description:

*General description.*—Strong flower consisting of tube bearing five sepals, five petals and many threadlike membranes (together, the corona) above which are five prominent anthers, the ovary and three prominent stigmas and styles.

*Buds.*—Shape: Obconical; apex is rounded, sepal awns extending up to 5.0 mm; base is rounded. Length: Approximately 6.0 cm. Diameter: Approximately 3.0 cm. Color: Commonly near Yellow-Green Group 144B.

*Flowers.*—Quantity: On average 4 to 12 flowers per plant. Depth: 6.0 cm. Diameter: 8.0 cm. Facing Direction: Outwardly and upwardly facing. Persistent or self-cleaning: Petals self-cleaning. Fragrance: Slightly sweet.

*Petals.*—Quantity: 5 alternating with sepals. Shape: Narrowly ovate. Petal margin: Entire. Petal length: 4.0 cm. Petal width: 1.5 cm. Petal texture of upper surface: Smooth. Petals texture of lower surface: Smooth. Color: of upper surface: Commonly near Green-White Group 157B. Color of under surface: Commonly near Green-White Group 157B. Apex: Rounded. Base: Truncate.

*Corona.*—General Description: Consists of two layers of rod-like filaments. Filament Quantity: Approximately 70 per layer. Filament Shape: Primarily ear, curling at the tip. Filament length: Approximately 1.5-2.0 cm. Filament width: Approximately 1.0 mm. Filament color: Commonly ⅔ of the length is near Purple Group 79A, the last ⅓ of the tip is near White Group 155C.

*Sepals.*—Quantity: 5. Shape: Narrow ovate. Margin: Entire. Sepal width: 5.0 cm. Sepal width: 1.5 cm. Sepal texture of upper surface: Smooth. Sepal texture of lower surface. Smooth. Apex: Rounded (except for awns). Base: Truncate; sepal awn (attached to apex) is recurving crescent-like and length up to 5.0 mm. Color of upper surface: Commonly near Yellow-Green Group 144B. Color of under surface: Commonly near Yellow-Green Group 144A.

*Peduncle.*—Strength: Strong. Shape: Rounded. Angle of attachment, approximately 45° from stem. Length: Approximately 4.0 cm. Diameter: Approximately 3.0 mm. Texture: Glabrous. Color: Commonly near Yellow-Green Group 146B.

*Reproductive organs.*—Operculum: Inner corona of upright rod-like filaments arranged in tight concentric rings; filament length ranges between 1.0 mm and 2.0 mm. Diameter: Less than 1.0 mm; very numerous filaments, at least 145 in number per flower. Color: Commonly near Purple Group 79A. Androgynophore: Tubular. Diameter: 1.0 cm. Height: 1.5 cm. Color: 146B. Stamens: Number: 5, filaments flattened. Width: 7.0 mm. Length: 30.0 mm to 35.0 mm. Color: Commonly near Yellow-Green Group 144D with light speckling near Purple Group 79A towards anther attachment. Anthers: Shape: Elliptic. Length: 45.0 mm. Width: 15.0 mm. Color: Commonly near Yellow-Green Group 150C. Attachment: Loosely minutely attached. Pollen: Amount: Moderate. Color: Commonly near Yellow Group 3C. Ovary: Position: Superior. Shape: ellipsoidal. Diameter: 18.0 cm. Surface texture: Smooth. Color: Commonly near Greyed-Yellow Group 160C. Styles: Strong, rigid, joined above ovary. Number: 3. Length including stigma: 4.0 cm. Color: Commonly near Purple Group N79B. Stigma: Bifurcated. Width: 2.0 cm. Depth: 0.5 cm. Color: Commonly near Yellow-Green Group 144D with mottling of near Greyed-Purple Group N187A.

*Fruit.*—Shape: Ovoid: Approximately 6 produced per plant. Ripened Fruit surface color: Commonly near Violet-Blue Group N92 to Purple Group N77B. Length: 9.0 cm. Width: 8.0 cm. Flesh color: Commonly near Purple Group N77B with an innermost pith color near White Group 155C. Fruit flavor and texture: Sweet to sour flavor with a silky texture and strong seeds.

*Seed.*—Number: 47: Shape: Oval. Length: less than 1.0 mm. Width: Less than 1.0 mm. Color: Commonly near Greyed-Orange Group 164A. Pulp color: Commonly near Yellow-Orange Group 17A.

Disease and pest resistance: Resistance to pathogens and pests common to *Passiflora* has not been observed.

The new cultivar has not been observed under all possible environmental conditions to date. Accordingly, it is possible that the phenotype may vary somewhat with variations in the environment, such as temperature, light intensity, and day length, without, however, any variance in genotype.

We claim:

1. A new and distinct cultivar of *Passiflora* plant named 'Wellington 101' characterized by the following combination of characteristics:

a) forms large white flowers consisting of white petals, green sepals, and deep purple colored corona filaments, b) exhibits dark green colored foliage, c) provides large round fruit with orange flesh, and d) exhibits a moderately vigorous, vining growth habit;

substantially as herein illustrated and described.

* * * * *